(12) United States Patent
Yun

(10) Patent No.: US 9,964,493 B2
(45) Date of Patent: May 8, 2018

(54) MECHANOLUMINESCENCE PAINT SENSOR FOR STRESS AND CRACK VISUALIZATIONS

(71) Applicant: GunJin Yun, Seoul (KR)

(72) Inventor: GunJin Yun, Seoul (KR)

(73) Assignee: The University of Akron, Akron, OH (US)

( * ) Notice: Subject to any disclaimer, the term of this patent is extended or adjusted under 35 U.S.C. 154(b) by 0 days. days.

(21) Appl. No.: 14/917,978

(22) PCT Filed: Sep. 10, 2014

(86) PCT No.: PCT/US2014/054925
§ 371 (c)(1),
(2) Date: Mar. 10, 2016

(87) PCT Pub. No.: WO2015/038594
PCT Pub. Date: Mar. 19, 2015

(65) Prior Publication Data
US 2016/0216211 A1    Jul. 28, 2016

Related U.S. Application Data

(60) Provisional application No. 61/875,751, filed on Sep. 10, 2013.

(51) Int. Cl.
| | | |
|---|---|---|
| G01B 11/16 | (2006.01) |
| G01N 21/70 | (2006.01) |
| C09K 11/02 | (2006.01) |
| C09D 5/22 | (2006.01) |
| C09K 11/77 | (2006.01) |
| F21K 2/04 | (2006.01) |
| C09K 11/57 | (2006.01) |
| G01L 1/24 | (2006.01) |
| G01N 21/88 | (2006.01) |

(52) U.S. Cl.
CPC .............. *G01N 21/70* (2013.01); *C09D 5/22* (2013.01); *C09K 11/02* (2013.01); *C09K 11/574* (2013.01); *C09K 11/7721* (2013.01); *C09K 11/7734* (2013.01); *C09K 11/7792* (2013.01); *F21K 2/04* (2013.01); *G01L 1/24* (2013.01); *G01N 21/8803* (2013.01)

(58) Field of Classification Search
CPC ... C09K 11/7792; C09K 11/02; C09K 11/574; C09K 11/7721; C09K 11/7734; C09D 5/22; F21K 2/04; G01L 1/24; G01N 21/70; G01N 21/8803
USPC .......................................................... 356/32
See application file for complete search history.

(56) References Cited

U.S. PATENT DOCUMENTS

| | | | | |
|---|---|---|---|---|
| 5,817,945 A * | 10/1998 | Morris | .................... | G01L 11/02 73/762 |
| 7,307,702 B1 * | 12/2007 | Mathur | ..................... | G01L 1/24 356/32 |
| 8,128,839 B2 | 3/2012 | Xu | | |
| 2001/0008445 A1 * | 7/2001 | Ifju | ........................ | G01B 11/20 356/32 |
| 2005/0224760 A1 * | 10/2005 | Xu | ....................... | C09K 11/574 252/301.4 R |
| 2009/0067196 A1 | 3/2009 | Takada et al. | | |

OTHER PUBLICATIONS

Chao-Nan Xu, Yun Liu, Morito Akiyama, Kazuhiro Nonaka, Xu-Guang Zheng, "Visualization of stress distribution in solid by mechanoluminescence", Proc. SPIE 4448, Optical Diagnostics for Fluids, Solids, and Combustion, (Nov. 26, 2001); doi: 10.1117/12.449400.*

* cited by examiner

*Primary Examiner* — Sunghee Y Gray
(74) *Attorney, Agent, or Firm* — Renner Kenner Greive Bobak Taylor & Weber

(57) ABSTRACT

A method of using a paint sensor to observe stress distributions of a stressed substrate includes the steps of applying a composition including a paintable medium and a mechanoluminescence material to a substrate, allowing the composition to form a solid film on the substrate, allowing the substrate to be stressed following the formation of the solid film, and measuring the stress the substrate has undergone by determining the mechanoluminescence of the solid film. A composition for visualizing stress or crack distributions includes a paintable medium and a mechanoluminescence material dispersed therein.

4 Claims, No Drawings

MECHANOLUMINESCENCE PAINT SENSOR FOR STRESS AND CRACK VISUALIZATIONS

CROSS-REFERENCE TO RELATED APPLICATION

This application claims priority to U.S. Provisional Patent Application No. 61/875,751 filed on Sep. 10, 2013, the contents of which are incorporated herein by reference.

FIELD OF THE INVENTION

The present invention generally relates to compositions comprising a paintable medium and a mechanoluminescence material. The present invention further relates to compositions that use mechanoluminescence to visualize stress or crack distributions. The present invention further relates to compositions comprising a mechanoluminescence material that are used on curved surfaces as a paint sensor.

BACKGROUND OF THE INVENTION

It is previously known to use mechanoluminescence materials for the visualization of stress or crack distributions through the use of mechanically-induced light emission. In many or all of these known applications of mechanoluminescence materials, the mechanoluminescence materials are mixed into compositions that are inflexible are otherwise unsuitable for applications such as use as a paint sensor. These prior art compositions also do not work well with applications that include complex shapes because the compositions are brittle.

Thus, there is a need in the art for improved mechanoluminescence materials that can be used for paint sensors. There is also a need in the art for mechanoluminescence materials that readily adhere and/bond to generally flat as well as curved surfaces and maintain structural integrity when the surfaces to which they adhere or bond bend or flex or are otherwise subjected to stress. There is a further need for improved mechanoluminescence materials that can transfer stresses to the mechanoluminescence materials for light emissions.

SUMMARY OF THE INVENTION

In a first embodiment, the present invention provides a method of using a paint sensor to observe stress distributions of a stressed substrate comprising the steps of providing a composition comprising a paintable medium and a mechanoluminescence material; applying the composition to a substrate; allowing the composition to form a solid film on the substrate; allowing the substrate to be stressed following the formation of the solid film; and measuring the stress the substrate has undergone by determining the mechanoluminescence of the solid film.

In a second embodiment, the present invention provides a method as in the first embodiment, wherein the paintable medium is an optical epoxy resin.

In a third embodiment, the present invention provides a method as in either the first or second embodiment, wherein the mechanoluminescence material is a plurality of mechanoluminescence particles selected from the group consisting of ZnS:Mn; $SrAl_2O_4$:Eu (SAOE); $SrAl_2O_4$:Eu,Dy (SAOED); $SrAl_2O_4$:Ce; $SrAl_2O_4$:Ce,Ho; $SrMgAl_6O_{11}$:Eu; $SrCaMgSi_2O_7$:Eu; $Sr_2MgSi_2O_7$:Eu; $Ca_2MgSi_2O_7$:Eu,Dy; $CaYAl_3O_7$:Eu; $Ca_2Al_2SiO_7$:Ce; and combinations thereof.

In a fourth embodiment, the present invention provides a method as in any of the first through third embodiments, wherein the step of allowing the composition to form a solid film involves drying a solvent from the composition, and wherein the dried solid film has a Shore D Hardness of from 60 to 95.

In a fifth embodiment, the present invention provides a method as in any of the first through fourth embodiments, wherein the dried solid film has a Shore D Hardness of 95.

In a sixth embodiment, the present invention provides a method as in any of the first through fifth embodiments, wherein the substrate includes one or more curved surfaces.

In a seventh embodiment, the present invention provides a method as in any of the first through sixth embodiments, wherein the step of allowing the substrate to be stressed includes applying a mechanical force to the substrate.

In an eighth embodiment, the present invention provides a method as in any of the first through seventh embodiments, wherein the step of allowing the substrate to be stressed includes allowing the stress to occur over a predetermined interval, and wherein the step of measuring the stress the substrate has undergone includes measuring the stress at the predetermined interval.

In a ninth embodiment, the present invention provides a composition for visualizing stress or crack distributions comprising a paintable medium and a mechanoluminescence material dispersed therein.

In a tenth embodiment, the present invention provides a composition as in the ninth embodiment, wherein the paintable medium is an optical epoxy resin.

In an eleventh embodiment, the present invention provides a composition as in either the ninth or tenth embodiments, wherein the mechanoluminescence material is a plurality of mechanoluminescence particles selected from the group consisting of ZnS:Mn; $SrAl_2O_4$:Eu (SAOE); $SrAl_2O_4$:Eu,Dy (SAOED); $SrAl_2O_4$:Ce; $SrAl_2O_4$:Ce,Ho; $SrMgAl_6O_{11}$:Eu; $SrCaMgSi_2O_7$:Eu; $Sr_2MgSi_2O_7$:Eu; $Ca_2MgSi_2O_7$:Eu,Dy; $CaYAl_3O_7$:Eu; $Ca_2Al_2SiO_7$:Ce; and combinations thereof.

In a twelfth embodiment, the present invention provides a method of using a composition as in any of the ninth through eleventh embodiments, comprising the steps of applying the composition to a substrate and allowing the composition to form a solid film.

In a thirteenth embodiment, the present invention provides a method of using a composition as in any of the ninth through twelfth embodiments, wherein the step of allowing the composition to form a solid film involves drying a solvent from the composition, and wherein the dried solid film has a Shore D Hardness of from 60 to 95.

In a fourteenth embodiment, the present invention provides a method of using a composition as in any of the ninth through thirteenth embodiments, wherein the dried solid film has a Shore D Hardness of 95.

In a fifteenth embodiment, the present invention provides a method of using a composition as in any of the ninth through fourteenth embodiments, wherein the substrate includes one or more curved surfaces.

In a sixteenth embodiment, the present invention provides a method of using a composition as in any of the ninth embodiments, further comprising the step of allowing a mechanical force to be applied to the substrate following the formation of the solid film.

In a seventeenth embodiment, the present invention provides a method of using a composition as in any of the ninth through sixteenth embodiments, further comprising the step of measuring the mechanical force the substrate has been subjected to by determining the mechanoluminescence of the dried solid film.

DETAILED DESCRIPTION OF ILLUSTRATIVE EMBODIMENTS

The present invention generally relates to compositions comprising a paintable medium and a mechanoluminescence material. The present invention further relates to compositions that use mechanoluminescence to visualize stress or crack distributions. The present invention further relates to compositions comprising a mechanoluminescence material that are used on curved surfaces as a paint sensor The present invention generally relates to compositions comprising mechanoluminescence (ML) material. The present invention further relates to compositions that use mechanoluminescence to visualize stress or crack distributions. The present invention further relates to compositions comprising ML material that are capable of being used in flexible applications as a paint sensor. Compositions of the present invention comprise a paintable medium and mechanoluminescence material dispersed therein. The mechanoluminescence material is preferably a plurality of mechanoluminescence particles. Mechanoluminescence is light emission resulting from any mechanical action on a solid. Compositions comprising ML material can be used as sensing materials that emit light in response to mechanical stress and deformation. It is preferred that the stress to be monitored is a dynamic stress instead of a static stress. Under static stress, the mechanoluminescent effect appears and then dissipates. However, under dynamic stress, the mechanoluminescent effect remains and gives a characterization of the dynamic stress. As described herein, compositions comprising ML material can be useful for the purpose of monitoring structural health parameters of those surfaces to which they are applied.

The paintable medium is any medium that is capable of being painted on a substrate through any known paint application technique. The paintable medium can be any liquid or liquefiable composition that, after application to a substrate in a thin layer, converts to form a solid film. In some embodiments, this formation of a solid film occurs by drying. Drying can refer to evaporation of a solvent, or can refer to oxidative cross-linking of a binder. This conversion can also be referred to as curing. In other embodiments, this conversion occurs as a chemical reaction, particularly as a polymerization.

In some embodiments, the formed solid film of the paintable medium is flexible as to be used on complex surfaces, such as curved surfaces, without cracking or becoming brittle after application. The paintable medium is capable of application to a surface through brush coating, spray paint, airspray, airless spray, roll coating, dip coating, and flow coating. The paint can also be made as a thin film. In some embodiments, a thin film is applied directly on a substrate. In other embodiments, a thin film is prepared independently of the substrate and then the thin film is applied to the substrate. In some embodiments, a doctor blade is used to produce a thin film.

The paintable medium comprises a binder or resin as the film-forming component of the medium. In some embodiments, the binder is selected from the group consisting of epoxy resin (also known as polyepoxides or epoxy polymers), optical epoxy resin, acrylic polymers, alkyd polymers, emulsion copolymers, and combinations thereof. In some embodiments, the formed solid film is optically transparent to more fully reveal the mechanoluminescent effects imparted by the ML particles dispersed in the paintable medium that forms the film.

In some embodiments, the paintable medium is an epoxy resin made from 1-chloro-2,3-epoxypropane and substituted phenols, such as bisphenol A. In one or more embodiments, the paintable medium is an optical epoxy resin commercially available from Gougeon Brothers, Inc. (Bay City, Mich.) as the West System® brand epoxy. In one or more embodiments, an optical epoxy resin is West System® 105 Epoxy Resin® with a hardener additive of West System® 206 Slow Hardener®. 105 Epoxy Resin® is a resin that is a clear, pale yellow, low-viscosity liquid epoxy resin. 105 Epoxy Resin® is formulated for use with West System® hardeners, can be cured in a wide temperature range to form a high-strength solid with excellent moisture resistance, is further formulated without volatile solvents, and does not shrink after curing. 105 Epoxy Resin® has a relatively high flash point and no strong solvent odor, making it safer to work with than polyester or vinylester resins. Resin viscosity of 105 Epoxy Resin® is approximately 1000 centipoise (cp) at 72 degrees F. (22 degrees C.). 206 Slow Hardener® is a low-viscosity epoxy curing agent for particular use when extended working and cure time is needed or to provide adequate working time at higher temperatures. In some embodiments, 206 Slow Hardener® is combined with 105 Epoxy Resin® in a five-part resin to one-part hardener ratio, and the cured resin/hardener mixture yields a rigid, high-strength, moisture-resistant solid with excellent bonding and coating properties.

In some embodiments, the paintable medium is an emulsion copolymer selected from the group consisting of styrene emulsion polymers, acrylic emulsion polymers, styrene/acrylic emulsion copolymers, and copolymers of ethenyl ethanoate (vinyl acetate) and a propenoate (acrylic) ester.

In some embodiments, the paintable medium comprises a solvent for thinning the medium. The solvent can be either an organic solvent or water. A solvent is utilized to reduce the viscosity of the paintable medium for improved application to a substrate.

The paintable medium must possess a viscosity in a range such that the ML material will disperse within the medium. In some embodiments, the ML material disperses as to form a generally consistent concentration of ML material throughout the paintable medium. If the viscosity of the medium is too high, the ML material will not disperse. If the viscosity of the medium is too low, the ML material will essentially precipitate from the medium.

The formed solid film must maintain a hardness sufficient for transferring the mechanical force from the formed solid film to the ML material. Mechanisms for the ML phenomena are best understood in the framework of a piezoelectrically induced detrapping model as understood by those skilled in the art. Therefore, it is important that the solid film is able to effectively transfer the stress to the ML material.

The paintable medium includes a mechanoluminescence (ML) material dispersed therein. In some embodiments, the ML material is a plurality of ML sensing particles. In some embodiments, the ML sensing particles are ceramic particles. The ML sensing particles can be provided in powder form and dispersed throughout the paintable medium so as to be dispersed throughout the solid film thereof once applied to a desired surface.

In some embodiments, the ML particles are selected from the group consisting of ZnS:Mn; $SrAl_2O_4$:Eu (SAOE); $SrAl_2O_4$:Eu,Dy (SAOED); $SrAl_2O_4$:Ce; $SrAl_2O_4$:Ce,Ho;

$SrMgAl_6O_{11}$:Eu;    $SrCaMgSi_2O_7$:Eu;    $Sr_2MgSi_2O_7$:Eu; $Ca_2MgSi_2O_7$:Eu,Dy; $CaYAl_3O_7$:Eu; $Ca_2Al_2SiO_7$:Ce; and combinations thereof.

The ML particles must have a diameter that is less than the thickness of the paint composition when it is applied to a substrate. In some embodiments, the ML particles have a mean diameter of from 200 nm or more to 40 microns or less. In some embodiments, the ML particles have a mean diameter of from 1 µm or more to 60 µm or less. In some embodiments, the ML particles have a mean diameter of from 2 µm or more to 20 µm or less. In some embodiments, the maximum diameter of the ML particles is 60 µm or less. In some embodiments, the maximum diameter of the ML particles is 20 µm or less.

Compositions of the present invention can be characterized by the mass ratio of the paintable medium to the ML material. In some embodiments, the mass ratio of the paintable medium to the ML material is from 1:1 or more to 3:1 or less. In some embodiments, the mass ratio of the paintable medium to the ML material is from 3:1 or more to 5:1 or less. In some embodiments, the mass ratio of the paintable medium to the ML material is 3:1 or approximate thereto. In some embodiments, the mass ratio of the paintable medium to the ML material is 2:1 or approximate thereto. In general, higher ratios show a higher sensitivity to stress.

ML materials can be characterized with respect to the wavelength of their excitation light. In some embodiments, this wavelength of excitation light is in a range from 400 nm or more to 1000 nm or less. In some embodiments, a peak wavelength of excitation light is 600 nm or approximate thereto. In some embodiments, a peak wavelength of excitation light is 520 nm or approximate thereto. Results show that SAOE and SAOED particles have a peak light intensity equal to a wavelength of 520 nm.

It is preferred that the ML material be well dispersed in the paintable medium. In some embodiments, the ML material can be dispersed uniformly in the paintable medium using a magnetic stirrer.

In some embodiments, the solid film formed from compositions of the present invention are flexible as to be used on complex surfaces, such as curved surfaces, without cracking or becoming brittle after application. A material is brittle if, when subjected to stress, it breaks without some deformation. Brittle materials can also be described as those where, upon application of stress, rupture occurs without any noticeable prior change in the rate of elongation. Herein, the formed solid films are not brittle and do not break apart after being applied to a substrate and subjected to stress. The flexibility of the formed solid film should also be such that the compositions can be accommodated on various substrates, such as wool, metal, concrete, ceramics, polymers, textiles, and biological tissues.

As discussed above, the film formed from compositions of the present invention should have sufficient strength and stiffness so as to transfer mechanical forces of stress (e.g. bending, sheering, axial, friction) to the ML material. This strength of the formed film can be characterized by Shore D Hardness. In some embodiments, the Shore D Hardness of the formed film is from 60 to 95. In some embodiments, the Shore D Hardness is from 75 to 95. In some embodiments, the Shore D Hardness of the formed film is 60 or higher. In some embodiments, the Shore D Hardness is 75 or higher. In some embodiments, the Shore D Hardness is 95 or approximate thereto.

In some embodiments, the formed solid film of a composition of the present invention is optically transparent so as to fully reveal the mechanoluminescent effects. In some embodiments, the transparency of a formed solid film is 90% or approximate thereto. In some embodiments, the transparency of a formed solid film is greater than 90%. In some embodiments, the formed solid film is transparent with respect to the wavelength of light that corresponds to the wavelength of light emitted from the ML material within the film when subjected to stress. In some embodiments, the formed solid film is generally optically transparent at wavelengths of from 400 nm or more to 1000 nm or less. In some embodiments, the solid film is generally optically transparent at a wavelength of 600 nm or approximate thereto. In some embodiments, the solid film is generally optically transparent at a wavelength of 520 nm or approximate thereto.

Formed solid films should have sufficient bonding strength with the substrate on which the compositions are applied. This can be further described as a formed solid film having sufficient peel strength as to remain bonded with a substrate.

In some embodiments, the amount of loading of the ML material in the formed solid film can be characterized by the ML material having a relatively constant concentration throughout the film. In some embodiments, the mass ratio of the formed solid film to the ML material is from 1:1 or more to 3:1 or less. In some embodiments, the mass ratio of the formed solid film to the ML material is from 3:1 or more to 5:1 or less. In some embodiments, the mass ratio of the formed solid film to the ML material is 3:1 or approximate thereto. In some embodiments, the mass ratio of the formed solid film to the ML material is 2:1 or approximate thereto.

In some embodiments, the formed film of a composition can be used in applications at temperatures of from −20 degrees Celsius or more to 50 degrees Celsius or less.

The formed films according to this invention can be employed for sensing and monitoring structural health of the surfaces to which they are applied. They can be used for routine inspection of structures, particularly for safety critical structures such as infrastructure and aircraft. They can also be utilized for applications relating to bioengineering and biomechanics.

The paint composition of this invention is applied to a desired substrate in order to observe and monitor the stresses applied to that substrate. The paint is applied and thereafter forms a solid film, as by drying, polymerizing, or as otherwise described above, on the desired substrate.

In one or more embodiments, the mechanoluminescence material requires an external light source to be placed into an excited state. In some embodiments, this light source is ambient or room lighting.

The mechanoluminescence of a formed solid film can be measured both qualitatively and quantitatively. The qualitative measurement for mechanoluminescence would be for whether light is present. The quantitative measurement for mechanoluminescence would be how much light is present. Both qualitative and quantitative measurements can be done using images and image processing. Examples of devices that can be used for such measurements include cameras, photo multiplier tubes, and spectrometers. Image processing can be used for measuring relative light intensity. For example, after an image is taken of the mechanoluminescence of a solid film, the color of the pixels can be analyzed. For a black and white image, the amount of white or gray color in an image will allow for the analysis of the mechanoluminescence. Further, photo multiplier tubes can measure light intensity over time. Also, standard curves can be constructed for converting light emission into a quantitative measurement. In some embodiments, mechanoluminescence of a formed solid film is measured by an apparatus as disclosed in U.S. Provisional Application 61/889,090, which is incorporated herein by reference.

Embodiments of the present invention include one or more methods of using a composition comprising a paintable medium and a mechanoluminescence material. A method of using a composition comprising a paintable medium and a mechanoluminescence material can include on or more of the following steps: providing a composition comprising a paintable medium and a mechanoluminescence material; applying the composition to a substrate; allowing the composition to form a solid film on the substrate; applying a mechanical force to the substrate to stress the substrate; measuring the mechanoluminescence of the solid film following the application of the mechanical force. Another method includes one or more of the following steps: applying a composition comprising a paintable medium and a mechanoluminescence material to a substrate to be observed for stress; allowing the composition to form a solid film; allowing a substrate to be stressed; and monitoring the substrate for stress by measuring the mechanoluminescence of the composition. Methods of the present invention can further include allowing the stress to occur over predetermined intervals and subsequently monitoring the stress at the predetermined intervals by measuring the mechanoluminescence. Such predetermined intervals can be further established as a method for routine monitoring of a substrate that undergoes stress.

The present invention offers one or more of the following advantages: flexibility of a formed solid film, crack damage visualization, stress distribution visualization, and easier application to a substrate.

EXAMPLE

Example 1

As one example for demonstrating the present invention, commercial SAOED powder materials (LumiNova® G-300M, United Mineral & Chemical Corporation) were used to manufacture thin ML sensing film. The SAOED powder was mixed with a commercial optical epoxy resin (West System® 105 Epoxy Resin® and West System® 206 Slow Hardener®) and thin ML sensing film with a thickness of 0.02 inches was manufactured by the doctor blade method. The mass ratio of the epoxy resin to the SAOED powder was 3:1, and the powder was dispersed uniformly in the epoxy using a magnetic stirrer. Standard dog-bone shaped aluminum (Al) specimens were coated with the cut ML sensing film by using a commercial adhesive (M-Bond 200 from Micro-Measurements). During tension tests of the coated Al specimens, images were obtained at a fixed frame per second by using a charge-coupled device (CCD) camera (AVT Manta G-033B) with a consistent gain level setting, and Vision Builder AI software (National Instruments) was used for capturing the images. The camera was positioned approximately 26 cm from the specimen with an exposure time of 0.1 ms and 10 fps. Using an Instron digital input/output board, the CCD camera and controller of the Instron testing machine (220 kips) were synchronized to achieve a perfect coincidence between the captured images and the load step data.

Once the images and the load step data were obtained, MATLAB® software was used to carry out the image processing. In the first step of the image processing, all images were sorted by time. The gray level images were then read and converted to pixel values. An area on the ML film image was selected, and the average value of light intensities in the area was used for calculations. The area integration of the gray level value on the specimen divided by the region of interest yields an average value of the ML light intensity corresponding to the stresses acting on the ML film. Since the frame rate was fixed at 10 fps, light intensity versus time could be drawn for each time step (0.1 s). This data was synchronized with the load step data to obtain the light intensity-force (i.e. stress) curves.

The ambient light from the environment was completely blocked to minimize errors and inconsistencies of the ML light intensity during the test. The ML sensing film was consistently excited with a 40-watt commercial lamp; two minutes was sufficient for acquiring fully photoexcited ML light intensity. However, even if it is not fully photoexcited (i.e. charged), the ML sensing film can still emit light under mechanical stresses because the mechanical stress is one of the excitations that generate separated charges (i.e. electrons-holes) similar to photoexcitation. If it was not fully photoexcited, changes of the ML light intensity may not be consistent due to different initial ML light intensity and effects of stress-free PL decay. Therefore, before any tests were carried out, the ML sensor was fully photoexcited. The wavelength of the excitation light source was between 400 and 1000 nm and the wavelength peak was around 600 nm. After full excitation, stress-free persistent luminescence (PL) light was emitted that displayed a naturally decaying intensity with respect to time. The maximum load was limited to 15 kN (230 MPa on an aluminum specimen) so that the aluminum specimen was within the linear elastic range. The maximum load was applied at different strain rates and different stress-free PL decay time intervals. For example, after full photoexcitation of the ML sensing film, the different time intervals were elapsed until the onset of the loadings.

In light of the foregoing, it should be appreciated that the present invention significantly advances the art by providing an improved compositions comprising a paintable medium and a mechanoluminescence material and associated methods of use. While particular embodiments of the invention have been disclosed in detail herein, it should be appreciated that the invention is not limited thereto or thereby inasmuch as variations on the invention herein will be readily appreciated by those of ordinary skill in the art. The scope of the invention shall be appreciated from the claims that follow.

What is claimed is:

1. A method of using a paint sensor to observe stress distributions of a stressed substrate comprising
   providing a composition comprising a paintable medium and a mechanoluminescence material;
   applying the composition to a substrate having one or more curved surfaces;
   allowing the composition to form a flexible solid film on the substrate, wherein the flexible solid film is optically transparent at wavelengths from 400 nm to 1000 nm; and
   allowing the flexible solid film on the substrate to be stressed, thereby allowing the flexible solid film to visualize crack distributions within the substrate by mechanoluminescence of the flexible solid film.

2. The method of claim 1, wherein the step of allowing the substrate to be stressed includes applying a mechanical force to the substrate.

3. The method of claim 1, wherein the step of allowing the substrate to be stressed includes allowing the stress to occur over a predetermined interval, and wherein the crack distributions are observed over the predetermined interval.

4. The method of claim 1, wherein the solid film does not crack or become brittle following said step of allowing the substrate to be stressed.

\* \* \* \* \*